US012758467B2

(12) United States Patent
Spallek et al.

(10) Patent No.: US 12,758,467 B2
(45) Date of Patent: Oct. 13, 2026

(54) CONTAINER

(71) Applicant: kocher-plastik Maschinenbau GmbH, Sulzbach / Laufen (DE)

(72) Inventors: Michael Spallek, Ingelheim (DE); Johannes Geser, Gerlingen (DE)

(73) Assignee: Rommelag Engineering GmbH, Sulzbach-Laufen (DE)

( * ) Notice: Subject to any disclaimer, the term of this patent is extended or adjusted under 35 U.S.C. 154(b) by 100 days.

(21) Appl. No.: 18/866,670

(22) PCT Filed: May 10, 2023

(86) PCT No.: PCT/EP2023/062465

§ 371 (c)(1),
(2) Date: Nov. 18, 2024

(87) PCT Pub. No.: WO2023/222484

PCT Pub. Date: Nov. 23, 2023

(65) Prior Publication Data

US 2025/0332065 A1 Oct. 30, 2025

(30) Foreign Application Priority Data

May 19, 2022 (DE) ..................... 10 2022 001 757.1

(51) Int. Cl.
*A61J 1/06* (2006.01)
*A61M 39/26* (2006.01)

(52) U.S. Cl.
CPC .............. *A61J 1/065* (2013.01); *A61M 39/26* (2013.01)

(58) Field of Classification Search
CPC A61J 1/065; A61J 1/067; A61J 1/1481; A61J 1/2037; A61J 1/2089; A61M 39/26; B65D 47/2068; B65D 1/095
See application file for complete search history.

(56) References Cited

U.S. PATENT DOCUMENTS 5,006,118 A 4/1991 Yule
5,390,898 A 2/1995 Smedley
5,423,791 A 6/1995 Bartlett
5,871,110 A * 2/1999 Grimard .............. A61J 1/2096 215/310
9,345,642 B2 * 5/2016 Heath ................... A61J 1/2096
9,345,643 B2 * 5/2016 Okiyama ............. A61J 1/2096
(Continued)

FOREIGN PATENT DOCUMENTS

WO 2015185187 A1 12/2015
WO 2016032814 A1 3/2016

OTHER PUBLICATIONS

Search Report for International Application No. PCT/EP2023/062465, 9 pp. Sep. 27, 2023.

*Primary Examiner* — Shawn M Braden
(74) *Attorney, Agent, or Firm* — Slayden Grubert Beard PLLC

(57) ABSTRACT

Disclosed is a container, such as a filled and closed ampoule, comprising at least one plastic material, having a container part for receiving container contents and having ahead part which can be separated from the container part along a separation point and which is integrally connected to the container part before separation, wherein the container has a valve device which, in its closed position, blocks a fluid-conducting connection into the container part and, in its open position, releases this connection.

19 Claims, 2 Drawing Sheets

(56) References Cited

U.S. PATENT DOCUMENTS

| | | | | |
|---|---|---|---|---|
| 10,271,935 | B2 * | 4/2019 | Bow | A61C 19/066 |
| 2017/0113829 | A1 | 4/2017 | Geser | |
| 2020/0164563 | A1 * | 5/2020 | Spallek | B65D 1/09 |
| 2020/0276081 | A1 * | 9/2020 | Geser | A61J 1/1481 |

* cited by examiner

CONTAINER

CROSS-REFERENCE TO RELATED APPLICATIONS

This application claims priority to German Patent Application No. DE 10 2022 001 757.1, filed on May 19, 2022 with the German Patent and Trademark Office. The contents of the aforesaid Patent Application are incorporated herein for all purposes.

BACKGROUND

This background section is provided for the purpose of generally describing the context of the disclosure. Work of the presently named inventor(s), to the extent the work is described in this background section, as well as aspects of the description that may not otherwise qualify as prior art at the time of filing, are neither expressly nor impliedly admitted as prior art against the present disclosure.

The disclosure relates to a container, particularly an ampoule, consisting of a plastics material, having a container part for receiving a container content and having a head part that can be separated from the container part along a separation point, said head part being integrally connected to the container part.

EP 1 989 117 B1 discloses a container comprising:

- a hollow receiving body for receiving a dispensing medium,
- a dispensing opening formed on the receiving body for dispensing the dispensing medium from the receiving body, and
- a closure part, which, outside the receiving body, comprises a hollow chamber keeping clear the dispensing opening and forms a head part of the container, wherein
- the closure part is detachably connected to the receiving body by means of a separation point and comprises wall parts facing one another in the region of the hollow chamber.

Due to the fact that, in the known solution, the wall parts of the closure part that are opposite one another are pressed into the hollow chamber, spaced apart from the separation point, such that the remaining free chamber cross-section of the hollow chamber with its receiving volume is reduced such that the dispensing medium stored in the receiving body cannot penetrate the hollow chamber, the dispensing medium in the container remains in the hollow receiving body, even in the form of a very thin liquid medium, and as such does not pass into the hollow chamber, with the result that said medium is also unable to escape from the container for removal which a process, is particularly disadvantageous if precise dosing is required when dispensing or the dispensing medium itself is very expensive or if precise mixing ratios and concentrations are required for subsequent applications when dispensing suspensions.

SUMMARY

A need exists to provide an improved solution for a container. The need is addressed by the subject matter of the independent claim(s). Embodiments of the invention are described in the dependent claims, the following description, and the drawings.

DESCRIPTION

Figure 1:
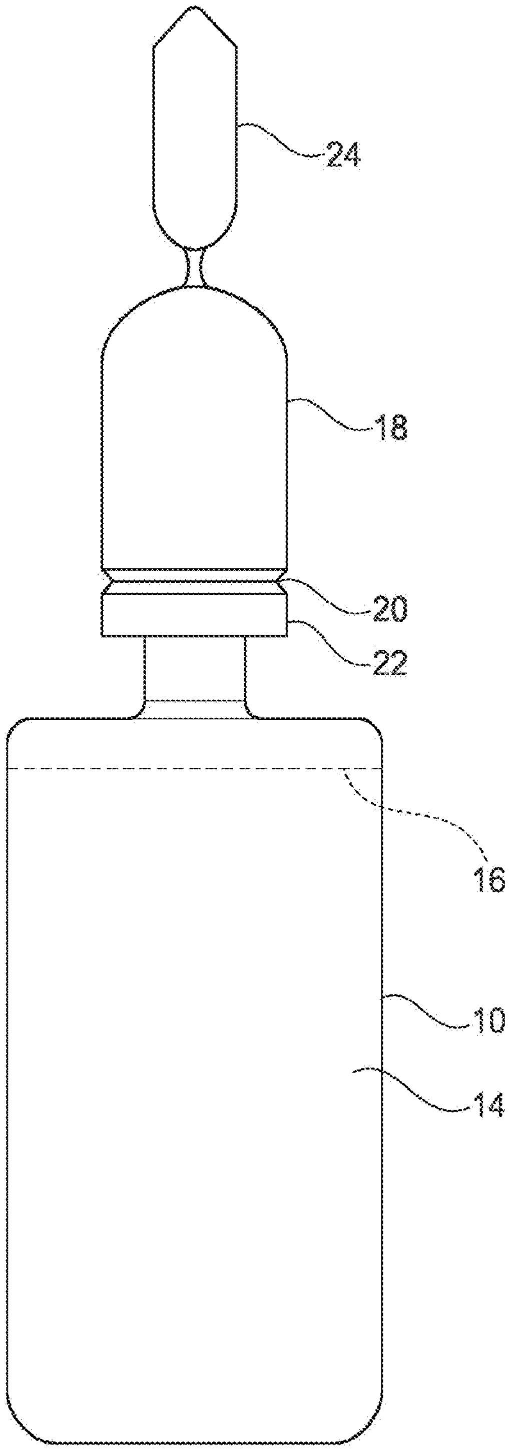
FIG. 1 shows a front view of an example filled container in the form of an ampoule.

The details of one or more embodiments are set forth in the accompanying drawings and the description below. Other features will be apparent from the description, drawings, and from the claims.

In the following description of embodiments of the invention, specific details are described in order to provide a thorough understanding of the invention. However, it will be apparent to one of ordinary skill in the art that the invention may be practiced without these specific details. In other instances, well-known features have not been described in detail to avoid unnecessarily complicating the instant description.

In some embodiments, a container (such as for example a filled and closed ampoule) comprises a valve device which, in its closed position, blocks a fluid-conducting connection into the container part and, in its open position, releases said connection, Accordingly, it is always possible to provide, when the container is in the closed state, that there is no undesirable transfer of fluid stored in the container, for example for medical purposes, towards the head part, which would otherwise lead to a change in the filling quantity on the side of the container part and the full container contents would then no longer be available for removal. As such, the head part is manufactured such that it generally comprises a hollow head space into which the content of the container part could pass without the valve device according to the teachings herein and would no longer be available if the head part were to be separated from the other container part for a removal process by means of a standard connection device. This is safely prevented with the container according to the teachings herein and as such the entire container contents are available for a removal process. Furthermore, the valve device is received in the closed container in a microbiologically safe manner.

After separating the head part, the valve device, which is initially closed, further provides that the content of the container part remains sealed in a microbiologically safe manner with respect to the environment, and, only when the valve device has been released, usually via a connection or removal device, such as a syringe body, the container contents pass in a microbiologically safe manner, without piercing a sealing element—which always entails the risk of generating particles—from the container into the syringe body. In a similar manner, a microbiologically safe multipart removal is possible as the valve device automatically safely closes the container after removing the removal device. This therefore has no parallel in the prior art.

In some embodiments of the container, it is provided that the valve device is arranged inside the container wall between the container part and the head part, for example in a neck part between the container part and the head part, and that, after separating the head part, the valve device is exposed for actuation. Due to its one-piece construction, the container is tightly hermetically and microbiologically sealed before separating the head part. Even after separating the head part along the separation point, a tight seal remains with respect to the environment due to the closed valve device.

In some embodiments of the container, it is provided that the valve device comprises an actuatable valve body for receiving the fluid-conducting connection, said valve body blocking the fluid-conducting connection in an original position under the influence of a resetting force. For example, in this case, the valve body is at least partially deformable to receive the resetting force and/or can be reset to its original blocking position by means of a resetting device, for example in the form of an energy accumulator. In such a way, the valve body, as a result of its inherent elasticity and/or under the influence of an external force actuation, once again, by itself, returns to its original blocking position and hermetically seals the container contents. The corresponding solution can be produced in a space-saving manner which means that the valve solution can also be used for small ampoule sizes.

In some embodiments of the container, it is provided that the valve device can be actuated by a connection device, for example in conical form, and passes in such a way from the blocking position to an open position in which the fluid-conducting connection is established for the purpose of removing the container fluid or introducing another fluid from or into the container part. Using the connection device, container fluid can be removed in the customary manner from inside the container part when the valve device is opened; however, it is also possible to introduce a different fluid, for example to produce a mixture or suspension, into the container part via the connection device, but only when the valve device is unlocked, and to prepare the medicine for a final removal operation in situ in the open container with a predefinable mixing ratio.

The valve device for example comprises an insert that comprises a connection point, for example in the form of a port for conical connections, such as tapered connections, so that the connection device can be attached such that it can be detached again. Corresponding connection fittings with connection devices such as syringe bodies, etc., for example, are known in technical jargon as Luer or Luer lock fittings. As such, two functions 'connection and valve mechanism' are combined in one container component.

In some embodiments of the container, it is provided that the insert extends between adjacent wall parts of the container part and the head part when the container is in the closed state and the separation point surrounds the insert on its outer circumferential side. While it is possible for an inherently elastically deformable valve body inserted directly into the container to abut the container wall thereof, it is possible to provide an insert with the valve device, wherein the insert, which is for example designed to be inherently stable, protects the valve body of the valve device from operator error and, due to the predefinable inherent stability of the insert, this can be incorporated in the container as a third component before sealing, but after filling of said container, as part of the blow moulding, filling and sealing manufacturing process. Furthermore, the separation point may be supported on the insert, which facilitates the opening process by removing the head part.

In some embodiments, it is for example provided that the connection point and access to the valve device are exposed when the head part is removed, the insert being securely fixed and connected to the inside of the container part. As such, it is possible to ensure secure positioning of the valve device in the region of the neck part as the transition point between the container part and the head part. After removing the head part, the connection point for attaching the connection device is exposed, with the result that, viewed from outside, a secure, fluid-tight connection is established between the connection device and the container content via the valve device.

In some embodiments of the container, it is provided that the insert is formed in multiple parts. Due to the multi-part structure of the insert, said insert is designed in a modular manner in the form of a modular system and different designs of valve devices with their valve bodies can be combined, substantially without restriction, with the respective insert receiving said valve devices such that a plurality of different valve devices can if necessary be produced for a container with various types of connection points, although said connection points are standardized, for example with regard to the connection device used in each case, such as a syringe body.

To provide further enhanced microbiological safety, it may also be provided that, after removing the head part, the exposed end face of the valve device is freely accessible, for example for carrying out disinfection, or for carrying out disinfection by wiping. Accordingly, it may also be provided that, after removing the head part, the free end face of the valve device optionally comprises a removable cover, for example in the form of a detachable film.

The disclosure also relates to a multi-component system, for example for a container as described above, consisting of a valve device with a resettable valve body, said device being received in an insert. Furthermore, the insert for example comprises a connection point for attaching a connection device. The corresponding multi-component system can be manufactured separately as a commercial product in a plurality of different configurations and only later connected to the wall material of the container in a suitable manner as part of the manufacturing process for the container, particularly in the form of a blow moulding, filling and sealing process.

To this extent, the disclosure also relates to a corresponding manufacturing method, wherein for example the specified multi-component system is inserted in the container in a form-locking manner after filling the container part and for example sealed, covered by a head part which can be separated from the container part via a separation point.

The container is for example filled with a fluid, particularly for medical purposes, said fluid optionally being able to contain a preservative. Furthermore, the container comprises, at least on the inside of the container part, for example one layer comprising cyclic olefin polymer and/or one layer comprising cyclic olefin copolymer. The insert and/or the valve device consists largely of polyolefin plastics such as polyethylene (PE) and/or polypropylene (PP) and/or cyclic olefin polymers (COP) and/or cyclic olefin copolymers (COC).

The container is discussed in greater detail below with reference to further embodiments according to the FIGS. The FIGS. are schematic and not necessarily to scale. Specific references to components, process steps, and other elements are not intended to be limiting. Further, it is understood that like parts bear the same or similar reference numerals when referring to alternate FIGS.

FIG. 1 shows, in its entirety, a filled container in one piece before opening, particularly in the form of an ampoule, consisting of plastics material, having a container part 10 for receiving a container content 14 that can be dispensed by means of the container for medical or other similar purposes. In FIG. 1, the container is shown in its vertical position and the height of the filling level of the container content 14 in the container part 10 is indicated by a dashed filling level line 16. The container content 14 is usually formed by a fluid, for example in the form of a liquid for medical purposes; however, it is also possible to provide paste-like media as the container content 14.

Viewed in the direction shown in FIG. 1, towards the top the container comprises a head part 18, which can be separated from the container part 10 along a separation point 20. Beneath the head part 18, a neck part 22 represents a transition between the container part 10 and the head part 18. The head part 18 comprises on its upper side a handle 24, which, in technical jargon, is referred to as a twist-off toggle, with which the head part 18 can be removed from the neck part 22 or container part 10 respectively along the separation point 20 with minimal actuating torques or actuating forces respectively. The corresponding structure is standard in such containers, such as ampoules manufactured using the BFS process, so this is not covered in further detail at this juncture.

Figure 3:
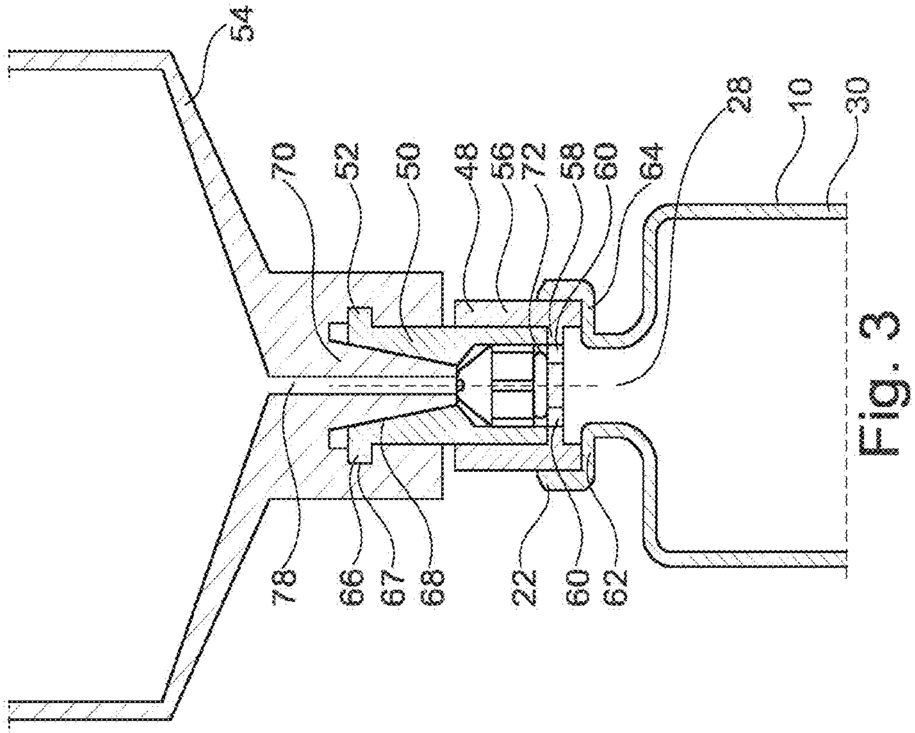
FIG. 3 shows the container according to FIG. 2 in the open state, after removing a head part, in a removal position in which the valve device is brought into the open position by a connection device placed thereon from outside.
Figure 2:
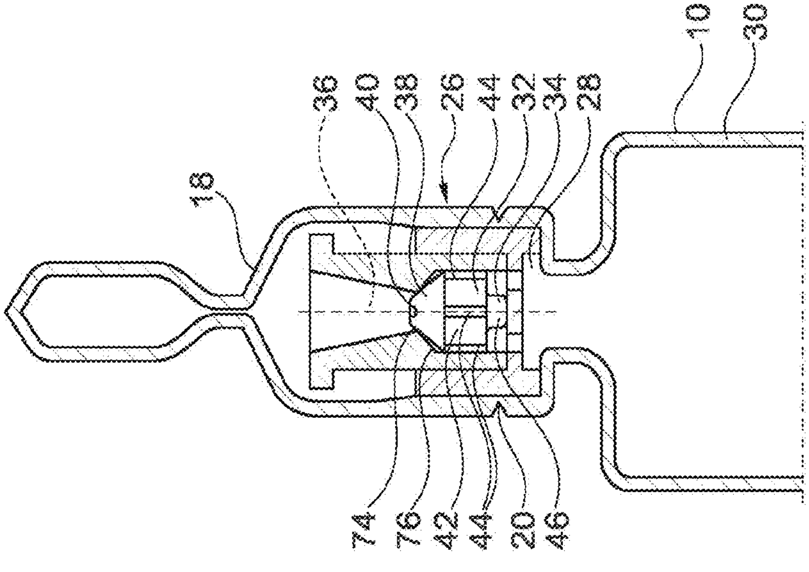
FIG. 2 is a longitudinal section showing the upper region of a corresponding example container, as viewed in the direction shown in FIG. 1, with a valve device in the non-actuated state.

As shown in FIGS. 2 and 3 in particular, the container comprises a valve device referred to in its entirely as 26, said device, in its closed position as shown in FIG. 2, blocking a fluid-conducting connection 28 into the container 10 and, in its open position, releasing said connection as shown in FIG. 3. As further shown in FIGS. 2 and 3, the valve device 26 is received inside the container wall 30 between the container part 10 and the head part 18, for example at least partially in the region of the neck part 22. After separating the head part 18 along the separation point 20 from the container part 10 above the neck part 22, the valve device 26 is then exposed on the end face for actuation.

The valve device 26 comprises an actuatable valve body 32 for receiving the aforementioned fluid-conducting connection 28, said valve body, being designed to be more or less flexible under the influence of a resetting force, which is permanently applied by means of a resetting device 34, being reset to its original blocking position as shown in FIG. 2. The valve body 32 can be moved downwards along an actuation axis 36 against the force of the resetting device 34 and in this manner moves out of its blocking position as shown in FIG. 2 into the open position shown in FIG. 3. The valve body 32 is configured to be substantially rotationally symmetrical with respect to the actuation axis 36 and comprises a conically tapering contact surface 38 in the direction of the handle 24, said contact surface enclosing an angle of inclination of approximately 45° in notional extension with the actuation axis 36. A radial overflow channel 40 is provided on the free end face of the valve body 32 and approximately in the centre thereof, protruding into the image plane in notional extension and accordingly transitioning into the conical contact surface 38 at its free ends. In this manner, the actuation axis 36 passes from above through the centre of the radial overflow channel 40 running horizontally in this case if the container assumes its vertical position shown in the figures. Otherwise, the valve body 32 is designed to run flat at its free end face up to the radial overflow channel 40 which is incorporated in a recessed manner.

Beneath the conically extending contact surface 38, the valve body 32 is configured to be cylindrical, wherein individual axial overflow channels 44 are incorporated in a recessed manner in the corresponding cylindrical lateral surface 42, said overflow channels permitting a fluid connection from the underside of the valve body 32 in the direction of the conical contact surface 38 and in the direction of the radial overflow channel 40. Otherwise, the cylindrical lateral surface 42 transitions seamlessly into the conical contact surface 38. Furthermore, on its underside, the valve body 32 comprises, as a resetting device 34, an elastically resilient element 46, which is for example an integral part of the valve body 32, and, for example, consists of a hollow plastics material moulded part, which is shown in its extended position in FIG. 2 and in its compressed position in FIG. 3, wherein, in the extended state of the element 46, the valve body 32 is in its closed position and in the compressed, actuated position it assumes its open position which releases the fluid-conducting connection 28. Instead of the solution shown, the elastically resilient element 46 may also be formed entirely from elastomer material, which is used as an insert part beneath the valve body 32. Further resetting devices 34 in the form of an energy accumulator, such as a helical spring, are possible if necessary.

The valve device 26 according to the present embodiment comprises an insert 48, which has a port 50 with a connection point 52 on the free end face of the port 50. The corresponding port 50 together with the connection point 52 is used to attach a connection device 54 such that it can be detached again, as is shown by way of example and in part in FIG. 3. The insert 48 consists substantially of a wall part 56 that forms a hollow cylinder, wherein the corresponding wall part 56 is integrally penetrated on the base or bottom side thereof by a transverse wall 58, which comprises a plurality of fluid passage points 60 as part of the fluid-conducting connection 28, which are arranged for example diametrically opposite one another with respect to the actuation axis 36 passing into the transverse wall 58. The wall part 56 running in a vertical direction when viewed in the direction of FIGS. 2 and 3 comprises an overhang beneath the transverse wall 58 and is securely connected to the container wall 30 on the free end face of the corresponding overhang by means of an annular weld seam 62, said container wall lying flush with the insert 48 at this point in the direction of a tapering 64 of the neck part 22. On its outer circumferential side, the cylindrical wall part 56 is surrounded by the separation point 20 when the container is in the closed state, said separation point in this case being formed by a weld along the insert 46. In this way, in the closed state, the outer circumferential side of the container wall 30 is fully in contact with the outer circumference of the insert 48, the upper region of the insert 48 with the wall part 56 being exposed after removal of the head part 18 as shown in FIG. 3.

The port 50 is received in its entirety in the insert 48, said port being integrally fixed in a defined manner with its outer circumference partially on the inner circumference of the insert 48. The port 50 comprises the connection point 52 on its free upper end face, said connection point showing only part of a screw thread 66 in the form of an outer thread in a simplified representation in FIGS. 2 and 3, the connection device 54 having a correspondingly formed inner thread 67 being able to be screwed onto said outer thread. The corresponding screw fitting thus forms part of a standardized Luer lock fitting. As the corresponding connection technology is standard in this field, further details are not provided at this juncture and reference is made to the relevant state of the art.

Furthermore, the port 50 comprises a conically extending recess 68 on its inner circumferential side, the corresponding recess 68 tapering conically in the direction of the valve body 32. As shown in FIG. 3, the conically extending recess 68 in the port 50 is thus used to insert a removal cone 70 of the connection device 54, in this case in the form of a so-called Luer lock syringe, said cone being intended to fit precisely. However, other connection devices with almost any configuration can also be connected to the opened container via the port 50, wherein the port 50 is for example used to receive tapered connections or other conically extending connection components.

The port 50 is configured to be cylindrical on the outer circumferential side up to the protruding outer thread with the respective screw thread 66 and is inserted such that it fits precisely in the inner circumference of the insert 48, wherein the bottom end of the port 50 thus lies on the top side of the transverse wall 58 and indeed such as to ensure in all cases that the fluid passages 60 are left clear. The port 50 thus forms, on its inner circumferential side, a kind of valve chamber 72 in which the valve body 32 is mounted such that it can be displaced longitudinally providing that the valve chamber 72 released by the valve body 32 in each displacement position of said body is part of the fluid-conducting connection 28 and is connected in a permanent fluid-conducting manner to the fluid passages 60 in the transverse wall 58.

Furthermore, the port 50 forms a valve sealing seat 74 opposite the contact surface 38 of the valve body 32. To form the valve sealing seat 74, the contact surface 38 may for example come into surface contact with t the inner wall surface, which is also conically inclined, of the port 50 at this point; for example, however, as shown in FIG. 2, it is provided that the contact cone 76 has a greater inclination on the inside of the port 50 than the cone for the contact surface 38, with the result that a linear valve seat compression arises with an increased sealing effect along the aforementioned valve sealing seat 74. Due to the linear valve sealing seat configuration, an unobstructed opening action for the valve body 32 is also achieved. At its widest upper point with the screw thread 66, the radial extension for the port 50 is always selected such that the head part 18 fits over the edge geometry of the insert 48 and the port 50 with a radial margin.

If the head part 18 is removed and the connection device 54 having the conical removal part 70 engages in the port 50, the valve body 32 is ejected through the free pointed end of the connection device 54 against the influence of the resetting device 34, with the result that fluid or the container content 14 respectively passes into the removal channel 78 of the connection device 54 via the fluid-conducting connection 28, said channel running concentrically with respect to the actuation axis 36 inside the connection device 54. Accordingly the fluid passes via the inside of the container part 10 and via the inside of the neck part 22 through the fluid passages 60 into the lower region of the valve chamber 72 and from there via the axial overflow channels 44 in the direction of the contact surface 38, which allows it to flow past laterally, held at a distance from the valve sealing seat 74, in the direction of the radial overflow channel 40, from where the liquid enters the removal channel 78. In this way, the free end of the removal cone 70, with contact on the end face, presses the valve body 32 against the influence of the resetting device 34, wherein the resetting force of the resetting device 34 increases accordingly. If the removal operation is at an end or initiated to the desired extent, the connection device 54 is unscrewed from the container again and the valve device 26 closes, wherein the inside of the container is in this way once again hermetically sealed with respect to the environment. In this way, it is generally also possible to admit fluid stored in the connection device 54 into the container via said connection device so as to mix said fluid with the fluid of the container content 14. Mixtures or suspensions of medicines can thus be produced in this way and then delivered in turn via the connection device 54, which is sensible when components need to be mixed together, yet their chemical properties mean that they cannot otherwise be stored together for long periods. The insert 48 used is multi-part, for example two-part in the present embodiment, wherein one insert part comprises the connection point 52 as the port 50 and the other insert part supports the separation point 20 in the form of the cylindrical wall part 56.

Due to this modular construction, it is also possible to use other valve devices 26, for example it would be conceivable, with an embodiment that is not shown, to place an elastically resilient valve body directly on the inner wall side of the container wall 30, which, in turn, actuated from outside via a connection device 54, releases a fluid path in the direction of the inside of the container part 10 in an elastically resilient manner and otherwise, reset by inherent elasticity, blocks the corresponding fluid path.

If, as shown in FIG. 3, the container is opened, in other words the head part 18 is removed, the free end face of the valve device 26 can be disinfected from outside, for example it can be disinfected by wiping. Furthermore, to ensure improved, microbiologically safe sealing, the valve device 26 may optionally comprise a removable cover (not shown), for example in the form of a detachable film.

The solution described above can be manufactured as part of a standard blow moulding, filling and sealing process and the use of insert bodies as part of such manufacturing processes is widely known in the art and disclosed in DE 10 2014 008 611 A1, for example.

For example, sterilised valve devices 26 are used in the filled BFS containers in a cleanroom environment, for example an isolator, for sterile products such as parenteral drugs. The valve device 26 is for example sterilised using high-energy radiation (for example in the form of gamma radiation, electron radiation, X-ray radiation or light), by autoclaving or by sterilising gases, such as ethylene oxide, chlorine dioxide, hydrogen peroxide, for example.

Furthermore-particularly for sterile products and products that are heat-treated for sterilisation purposes—the function of the valve device 26 is beneficial in the event that an excess pressure—due for example to temperature changes, air pressure changes during transport or mechanical forces on the container-arises in the container part 10.

For example, materials comprising cyclic olefin polymers (COP, manufactured by Zeonex) and/or cyclic olefin copolymers (COC, manufactured by Topas) are used as container materials, as well as outer material for the valve device 26. To the average person skilled in the art, it is surprising that these material combinations can be satisfactorily welded together in the BES process. BFS containers made from multi-layer plastics are also possible, as described by way of example in DE 10 347 908 A1.

For example, halogenated butyl rubbers, silicones or, for example, elastomer-modified cyclic olefin copolymers are used as elastomer material for the valve body 32, the latter materials being easy to manufacture by injection moulding.

Another aspect of the containers or ampoules respectively is that the space above and beneath the valve device 26 having the movable valve body 32 is surrounded by the same material, thus providing uniform permeation behaviour.

Therefore, overall, this provides a container solution, for example in the form of an ampoule, which is suitable for parenteral drugs and combines the following features in a beneficial manner:

integral tamperproof seal due to detachable head part, optional extra tamperproof seal due to detachable film on the valve device, the ampoule contents do not leak when removing the head part, ease of access without risk of particle formation as no cannulas, needles or similar items need to be used, safe sealing before and after each use (including waste disposal), simple optional disinfection by wiping before each removal and minimal losses due to water permeation during storage of the filled and sealed container, safe sealing even in the event of excess pressure in the container part.

This therefore has no parallel in the prior art.

The invention has been described in the preceding using various exemplary embodiments. Other variations to the disclosed embodiments may be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor, device, or other unit may be arranged to fulfil the functions of several items recited in the claims. Likewise, multiple processors, devices, or other units may be arranged to fulfil the function of several items recited in the claims.

The term "exemplary" used throughout the specification means "serving as an example, instance, or exemplification" and does not mean "preferred" or "having advantages" over other embodiments. The term "in particular" and "particularly" used throughout the specification means "for example" or "for instance".

The mere fact that certain measures are recited in mutually different dependent claims or embodiments does not indicate that a combination of these measures cannot be used to advantage. Any reference signs in the claims should not be construed as limiting the scope.

What is claimed is:

1. A container, comprising at least one plastics material, having a container part for receiving a container content and having a head part which can be separated from the container part along a separation point and which is integrally connected to the container part before separation, wherein the container has a valve device which, in its closed position, blocks a fluid-conducting connection into the container part and, in its open position, releases this connection; wherein the valve device is arranged inside a container wall between the container part and the head part, and wherein after separating the head part, the valve device is exposed for actuation.

2. The container of claim 1, wherein the valve device comprises an actuatable valve body for receiving the fluid-conducting connection, said valve body blocking the fluid-conducting connection in an original position under the influence of a resetting force.

3. The container of claim 1, not requiring the use of a cannula, needle or similar.

4. The container of claim 1, wherein the valve body is configured substantially rotationally symmetrical with respect to an actuation axis and has a conically tapering contact surface in the direction of a handle to separate the head part.

5. The container of claim 1, wherein a radially extending overflow channel is provided on a free end face of the valve body, which transitions into a conical contact surface at its free ends.

6. The container of claim 1, wherein beneath the conically extending contact surface, the valve body is configured to be cylindrical and wherein individual overflow channels are incorporated in a recessed manner in the corresponding cylindrical lateral surface, said overflow channels permitting a fluid connection from the underside of the valve body in the direction of the conical contact surface and in the direction of a radial overflow channel.

7. The container of claim 1, wherein to allow the valve device to receive a resetting force, the valve body is at least partially deformable and/or can be reset to its original blocking position using a resetting device.

8. The container of claim 1, wherein the valve device can be actuated by a connection device and passes in such a way from a blocking position to an open position in which the fluid-conducting connection is established for the purpose of removing and/or introducing a fluid from or into the container part.

9. The container of claim 1, wherein the valve device comprises an insert, which comprises a connection point to attach the connection device such that it can be detached again.

10. The container of claim 1, wherein an insert has a hollow-cylindrical wall part, which is integrally penetrated by a transverse wall at the foot or bottom side, said wall having a plurality of fluid passage points as part of the fluid-conducting connection.

11. The container of claim 1, wherein, when the container is in the closed state, an insert extends between adjacent wall parts of the container part and the head part and wherein the separation point surrounds the insert on its outer circumferential side.

12. The container of claim 1, wherein, when the head part is removed, the connection point and access to the valve device are exposed.

13. The container of claim 1, wherein an insert is securely connected to an inside of the container part.

14. The container of claim 1, wherein an insert is configured to be multi-part, and wherein one insert part comprises the connection point and the other insert part, supporting the separation point, at least partially surrounds the first insert part and comprises at least one through opening as part of the fluid-conducting connection, said opening establishing a permanent connection between the container part and a valve chamber with the valve body.

15. The container of claim 1, wherein, after removing the head part, a free end face of the valve device is freely accessible.

16. The container of claim 1, wherein, after removing the head part, a free end face of the valve device comprises a removable cover.

17. A multi-component system for a container of claim 1, comprising a valve device with a valve body, said valve device being received in an insert.

18. The multi-component system of claim 17, wherein the insert comprises a connection point for attaching a connection device.

19. A blow moulding, filling and sealing process for manufacturing a container with the multi-component system of claim 17, the container comprising: at least one plastics material, having a container part for receiving a container content and having a head part which can be separated from the container part along a separation point and which is integrally connected to the container part before separation, wherein the container is configured for a valve device which, in its closed position, blocks a fluid-conducting connection into the container part and, in its open position, releases this connection; the method comprising:

filling the container part; and inserting the multi-component system in a form-locking manner and covered by head part.

* * * * *